US009011898B2

(12) United States Patent
Curcio et al.

(10) Patent No.: US 9,011,898 B2
(45) Date of Patent: Apr. 21, 2015

(54) COMPOSITION FOR ACTIVE PRINCIPLES DELIVERY CONTAINING A FATTY ACID EXCIPIENT

(75) Inventors: Maria Curcio, Saluggia (IT); Ilaria Zambaldi, Ivrea (IT); Daniela Gramaglia, Ponderano (IT); Andrea Grignani, Chieri (IT)

(73) Assignee: CID S.p.A., Saluggia (Vercelli) (IT)

( * ) Notice: Subject to any disclaimer, the term of this patent is extended or adjusted under 35 U.S.C. 154(b) by 91 days.

(21) Appl. No.: 13/825,074

(22) PCT Filed: Sep. 19, 2011

(86) PCT No.: PCT/IB2011/054092
§ 371 (c)(1),
(2), (4) Date: Mar. 20, 2013

(87) PCT Pub. No.: WO2012/038881
PCT Pub. Date: Mar. 29, 2012

(65) Prior Publication Data
US 2013/0280315 A1   Oct. 24, 2013

(30) Foreign Application Priority Data
Sep. 20, 2010   (IT) .............................. TO2010A0766

(51) Int. Cl.
*A61L 31/16*   (2006.01)
*A61L 29/16*   (2006.01)
*A61L 27/54*   (2006.01)

(52) U.S. Cl.
CPC .................. *A61L 31/16* (2013.01); *A61L 29/16* (2013.01); *A61L 27/54* (2013.01); *A61L 2300/41* (2013.01); *A61L 2300/412* (2013.01); *A61L 2300/416* (2013.01); *A61L 2300/426* (2013.01); *A61L 2300/43* (2013.01); *A61L 2300/432* (2013.01); *A61L 2300/602* (2013.01)

(58) Field of Classification Search
CPC ......... A61L 27/54; A61L 29/16; A61L 31/16; A61L 2300/608; A61L 2300/61
See application file for complete search history.

(56) References Cited

U.S. PATENT DOCUMENTS

2006/0095123 A1   5/2006   Flanagan
2007/0202149 A1*  8/2007   Faucher et al. ............... 424/425

FOREIGN PATENT DOCUMENTS

CN            1256628 A        6/2000
EP          1 994 950 A2       11/2008
WO       WO 03/035134 A1       5/2003

OTHER PUBLICATIONS

Jan. 12, 2012 PCT Search Report for International Application No. PCT/IB2011/054092 (12 pages).
Abstract for CN1256628A (1 page), (Jun. 2000).

* cited by examiner

Primary Examiner — Carlos Azpuru
(74) Attorney, Agent, or Firm — Popovich, Wiles & O'Connell, P.A.

(57) ABSTRACT

Composition for delivery of at least one active principle at the implantation site of an implant device, including:
  at least one active principle, and
  at least a first excipient combined with the at least one active principle, wherein the at least a first excipient is selected among fatty acids with a linear or branched, saturated chain, including a number of carbon atoms between 14 and 36.

18 Claims, 3 Drawing Sheets

COMPOSITION FOR ACTIVE PRINCIPLES DELIVERY CONTAINING A FATTY ACID EXCIPIENT

FIELD OF THE INVENTION

The present description concerns compositions for delivery of active principles at the implantation site of an implant device.

TECHNICAL BACKGROUND

Implant devices, for example stents, can be used when the lumen of an artery undergoes a narrowing, for example provoked by an obstruction. Such obstruction results in decreased blood flow and can cause ischemic phenomena.

A stent is a cylindrical metallic structure that is introduced into the artery lumen and made to expand at the level of the obstruction until its diameter is equal to the original diameter of the vessel. In this way the vessel narrowing, i.e., stenosis, is reduced, both in the acute phase and in the long term.

Through the years, the principal function of the stent, as mechanical support of the vessel, was joined by a pharmacologic action to reduce the incidence of a phenomenon known as restenosis, which consists of partial or total reocclusion of the vessel.

The phenomenon is attributed essentially to the undesired proliferation of smooth muscle cells in the vessel walls that can be triggered by factors attributable to the procedural phase (excessive stress to the vessel wall) and/or to the implanted device (reduced biocompatibility of materials, suboptimal surface characteristics, excessive structural rigidity, etc.).

The association of active principles to implant devices with the object of limiting restenosis is an established technique Typical examples are the so-called Drug Eluting Stents (DESs), i.e., stents that carry pharmaceutical substances, such as agents that are antagonistic to restenosis, to the stent implantation site.

An active principle can be loaded onto implantable devices by means of compounds that act as vectors for them and that modulate their delivery in correspondence to the implantation site.

Although polymeric constituents have been used as vectors for delivery of active principles from, for example, coronary stents, several reasons for concern have now been raised regarding the safety of these materials.

For example, polymeric substances applied to an implantable device can remain in situ for very long periods of time, in this way disturbing or modifying the healing process at the implantation site in an undesirable way. This effect can be aggravated by incomplete delivery of the drug by the vector.

Such adverse reactions remain also when biodegradable polymers are used. In fact, the polymer always remains beyond the period of diffusion of the active principle and introduces the possibility of cytotoxic or inflammatory effects linked to in situ degradation of the polymeric vector (take, for example, the degradation of polyester-based polymers).

Compositions that are not polymeric in nature have been used for delivery of active principles, for example in the form of fatty acid esters of polyalcohols, sugars or vitamins as described in the European patent application EP-A-1 994 950.

The compositions described in EP-A-1 994 950 have been shown capable of regulating delivery of active principles by implanted devices and to avoid the long-term negative biological effects linked to the presence of polymeric vectors on the device itself.

Nevertheless, these solutions are not always satisfactory in terms of optimal modulation of active principle delivery by implanted devices and of applicability to the preparation of molecules particularly subject to degradation during the manufacturing process of the implantable device. In fact, the use of drugs that are extremely potent from a pharmacological point of view (e.g., antitumor or immunosuppressive drugs) require controlled delivery of the active principle that is prolonged over time, to prevent and/or reduce vessel restenosis, and that is very accurate also in the early phase of administration, controlling possible initial peaks of drug to avoid local toxic effects. On the other hand, the scarce stability of some drugs requires that the most gentle preparative conditions (temperature, mechanical stress, solvents, etc.) possible be used and therefore that suitable compositions are chosen for their loading on implant devices, for example stents.

SUMMARY OF THE INVENTION

Therefore, considering these premises, the need is felt for better, more efficacious solutions that provide compositions for delivery of an active principle or principles from implant devices capable of overcoming the disadvantages in the known art.

According to the invention, the above-said object is obtained by means of the solution specifically recalled in the attached claims, which constitute an integral part of the present description.

In one embodiment, the composition for delivery of at least one active principle at the implantation site of an implant device includes at least one active principle, and at least a first excipient combined with the at least one active principle, where the at least first excipient is selected among fatty acids with a linear or branched, saturated chain, including a number of carbon atoms between 14 and 36.

A second embodiment of the present description concerns a composition for delivery of at least one active principle at the implantation site of an implant device that includes at least one active principle, at least a first excipient and at least a second excipient different from the at least first excipient, combined with the at least one active principle, where the at least first excipient and the at least second excipient are selected among fatty acids with a linear or branched, saturated chain, including a number of carbon atoms between 14 and 36.

The results reported below demonstrate that the compositions described herein allow the preparation of devices without degradation of the drugs used and modulate the delivery of active principle with greater control of delivery, in particular in the initial phase, with respect to a composition including fatty acid esters according to the known art.

BRIEF DESCRIPTION OF THE FIGURES

The invention will now be described in detail, purely by way of non-limiting example with reference to the annexed drawings, in which.

DETAILED DESCRIPTION OF SOME EXEMPLARY EMBODIMENTS

Figure 1:
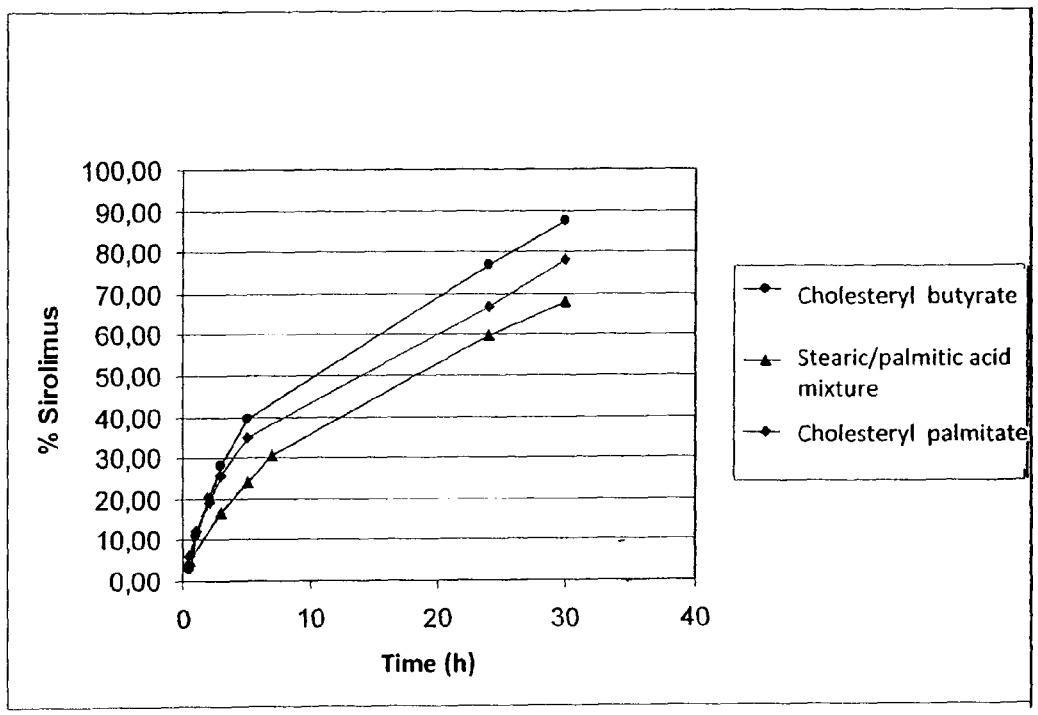
FIG. 1: Delivery profile of the Sirolimus:Cholesteryl butyrate compositions with a ratio of 45:55, w/w, and Sirolimus:Steric acid/Palmitic acid with a ratio of 45:55, w/w, loaded on a metallic stent.

The invention will now be described in detail, by way of non limiting example, with reference to compositions for delivery of active principle(s) from an implant device, such as for example, a stent possibly provided with reservoirs on its external or internal surfaces destined to contain the composition.

It is clear that the scope of this description is in no way limited to such use, since the compositions described herein can be used with any type of implant device, such as for example cardiac valve prostheses, angioplasty balloons.

Moreover, while the experimental data provided below refers to use of the compositions described herein for delivery of a lipophilic active principle, the scope of the present description is in no way limited to this specific type of active principle, because the compositions described herein have an excellent degree of compatibility with other types of active principles, such as for example hydrophilic compounds.

In the description that follows, numerous specific details are presented to provide a thorough understanding of the embodiment. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in a certain embodiment" in various places throughout this specification are not necessarily all referring to the same embodiment. Furthermore, the particular features, structures or characteristics may be combined in any suitable manner in one or more embodiments.

The headings provided herein are for convenience only and do not interpret the scope or meaning of the embodiments.

One embodiment of the present description concerns a composition for delivery of at least one active principle at the implantation site of an implant device including:
  at least one active principle, and
  at least a first excipient combined with the at least one active principle, said at least first excipient being selected among fatty acids with a linear or branched, saturated chain, including a number of carbon atoms between 14 and 36.

A second embodiment of the present description concerns a composition for delivery of at least one active principle at the implantation site of an implant device that includes at least one active principle, at least a first excipient combined with said at least one active principle and at least a second excipient different from said at least first excipient, combined with said at least one active principle, where the at least first excipient and the at least second excipient are selected among fatty acids with a linear or branched, saturated chain, including a number of carbon atoms between 14 and 36.

The compositions described herein are capable of modulating the delivery and, consequently, the bio-availability of the active principle(s)—i.e., of the "drug" or the "drugs"—loaded on the implant device. In particular, the compositions object of the present description are capable of prolonging for a long period of time (up to several months) the delivery of active principle(s) at the implantation site, rendering their vessel restenosis-antagonizing effect more effective. Added to this effect is a reduced deliver of drug(s) during the initial elution phase in order to avoid local toxic effects.

In particular, the compositions described herein provide delivery of the active principle(s) at the implantation site for a period comprised between 3 and 140 days.

In addition, the compositions described herein are completely released from the implant device in a period of time similar or equal to that of the complete release of the drug. Consequently, at the end of the elution process, the implant device becomes again a bare implant device and free of any residue.

The compositions described herein do not require in situ degradation phases to be released from the implant device to then be metabolised and/or excreted by the human body: as used herein, the expression "in situ degradation" is intended to indicate, in general, any modification of the composition before detachment or dissolution and removal from the surface of the implant device.

Preferred compositions as described herein envision the use, as excipients, of fatty acids with a linear or branched, saturated chain, preferably selected among stearic acid, palmitic acid, myristic acid, arachidic acid, behenic acid, melissic acid, more preferably among stearic acid and palmitic acid.

Fatty acids are constituents of tissues and are normally excreted from the human body or enter the normal metabolic cycles of the organism.

Stearic acid, in particular, is one of the most common saturated fatty acids in animals and plants. In the human body it is one of the major constituents of biological membranes.

Stearic acid is widely used in oral and topical pharmaceutical formulations, especially as lubricants and binders. It is also used in pharmaceutical products used in parenteral nutrition, in food preparation and in cosmetics.

Since such excipients leave the implant device, typically together with the active principle, they are also capable of modifying the "micro-environment" around the device and modulating the elution and diffusion of the active principle at the implantation site in an active way, influencing metabolic processes or acting as vehicles.

Without wishing to commit to any one theory, the Applicant has reason to believe that the use of one or more excipients consisting of fatty acids provides compositions having a substantially homogeneous structure, i.e., substantially free of cavities and/or microaggregates, characterised by active principle release kinetics that are controlled and continuous in time. In fact, cavities and/or microaggregates negatively affect how active principles are released, which may manifest for example as positive and/or negative peaks of release.

In addition, microaggregates and/or cavities/pores—characteristic of compositions containing fatty acid esters as excipients—cause reduced adhesion and/or physical instability (in time and/or following the solicitations or mechanical stress to which a stent is generally exposed) of the composition loaded onto the surface of the stent.

Again, saturated fatty acids have reduced steric hindrance with respect to that of fatty acid esters and at equal ratios (w/w) of excipient (i): active principle they provide more homogeneous dispersion of the active principle with the excipient (i) in the composition and consequently favour a more controlled delivery of the active principle at the implantation site.

In particular, the Applicant has observed that a non-homogeneous distribution of the composition in the reservoirs of the stent leads to delivery kinetics that are less controlled and continuous in time with respect to a uniform distribution, characteristic of compositions containing fatty acids.

Furthermore, the saturated fatty acids in general have a linear spatial configuration that allows them to be arranged in a more ordered way, making intermolecular interactions (hydrogen bonds and Van der Waals forces) more efficacious, and therefore providing compositions substantially free of structural defects such as porosity, cavities, etc., that negatively influence—as was already said—both the loading/stability of the composition on the implant device and the way that active principle is delivered from the device itself.

As will be evident from the examples provided below, the compositions described herein achieve the following results:
- they improve modulation of delivery of active principle from implant devices with respect to compositions comprising fatty acid esters as excipients, in particular they are able to extend the delivery of active principle for a long time (up to several months) and to avoid initial peaks of drug release.
- they have a substantially homogeneous structure, i.e., substantially free of molecular aggregates and/or cavities, permitting i) active modulation, preferably slowing down, of the release of active principle, and/or ii) better adhesion of the composition to the surface of the implant device.

Through their physical properties, the compositions described herein can, also, be stratified for example on the external and/or internal of a stent or inside a reservoir on the external and/or internal surface of the stent. This can be useful in preparing drug-eluting stents with layers that contain different drugs or the same drug with different delivery kinetic profiles.

In addition the Applicant believes, — without wanting to commit to any one theory—that the use of one or more excipients constituted of fatty acids provides greater stability of the active principle contained in the composition due to the greater number of free acid groups of the fatty acids with respect to those of the fatty acid esters.

In fact, fatty acids with chains of C14-C36 have an acid value (number of free acid groups) comprised between 100 and 250, while the acid value of the fatty acid esters is generally less than 10.

In particular, the use of fatty acids with a chain comprised between 16 and 36 carbon atoms provides an acidic microenvironment more favourable for the stability, for example of sirolimus.

Sirolimus—a drug having an anti-restenosis effect—is a molecule that is easily degraded and has a multitude of isomeric forms. Stability studies in aqueous solutions show that sirolimus is less stable in aqueous environments at neutral or basic pH with respect to aqueous environments at acidic pH.

Consequently, the Applicant has reason to believe that the presence of an elevated number of free acid groups in the composition object of the present description improves the stability of the active principle contained in the composition itself.

The compositions described herein can be prepared in powder form (with micrometric or submicrometric particle sizes), paste, solution, suspension, where such compositions are loadable on a stent according to techniques commonly known in the sector.

The ratio of drug:excipient(s) in the composition can be adjusted to obtain the desired drug delivery profile or to produce the desired effects on drug stability or on the physical state of the drug.

Also, the drug/excipient compositions can be subjected to stabilisation treatments, where stabilisation intends giving the composition properties of mechanical resistance and adhesion to the stent surface adequate for the mechanical stress incurred by the stent during the phases of transport, storage, the procedure of insertion into the vascular system and expansion.

The stabilisation/fixation treatments can be selected among exposure to heat, solvent dipping for controlled times, exposure to solvent spray or vapour, where the term "solvent" in the scope of the present description indicates a liquid with moderate capacity to dissolve the fatty acid and practically non toward the drug.

The compositions object of the present description permit, for example, subjecting the stent loaded with the composition to a stabilisation procedure by means of thermal treatment to a temperature in the order of 65-80° C., followed by cooling to ambient temperature.

Such temperature interval is inferior to the temperature necessary to stabilise compositions comprising fatty acid esters as excipients (in the order of 85-120° C.) and reduces the risk of degradation to the active principle.

The use of lower temperature for fixation of the composition in the reservoirs of the stent has the advantage of exerting less physical stress on the drug, thus guaranteeing greater integrity to it. High temperatures generally cause degradation of the drug and consequently loss of its therapeutic efficacy. Moreover, high temperature can trigger degradation processes discovered after time and that are accelerated by other types of physical stress (exposure to light, to humidity, etc.).

In addition, the present Applicant has observed that at the end of the stabilisation process by heat treatment at a temperature in the order of 65-80° C. the compositions appear as solid compositions in which the active principle and the excipients have assumed a crystalline structure with a nano-, micro-crystalline cluster habitus. The thermal cycles of heating to 65-80° C. and successive cooling to ambient temperature allow the active principle and the excipients of the composition to reorganise with a homogeneous nano-, micro-crystalline habit. Such crystalline reorganisation is not seen in the case of thermal cycles with heating to 85-120° C. and successive cooling to ambient temperature, because the accelerated kinetics of passing from the liquid phase to the solid produces different crystalline habits, with macro-aggregates, rough zones with cavities and/or pores and amorphous portions of the active principle.

Assumption of a crystalline form by the active principle and the excipients contributes to modulating the release of the active principle from the implant device with respect to a situation in which the active principle is in an amorphous structure. Amorphous substances with respect to the corresponding crystalline forms have peculiar characteristics linked to their internal "disorder": higher apparent solubility/dissolution rate, tendency to crystallize, greater reactivity in the solid state and greater hygroscopicity. The Applicant has observed that the delivery kinetics of the active principle in crystalline form is inferior to that in which the drug has an amorphous structure.

Therefore, when a stent loaded with the composition object of the present description is subjected to a stabilisation procedure using heat treatment at a temperature comprised between 65 and 80° C. and successively cooled to ambient temperature, a synergistic effect on active principle delivery kinetics is observed between the effect of the fatty acids and the crystalline form assumed by the active principle.

Drugs that are loadable onto an implant device, such as for example a stent, can be selected—without limitations—among the following classes: Anti-inflammatory agents, anti-proliferative agents, promoters of wound healing, corticosteroids, tyrosine kinase inhibitors, immunosuppressants and anti-tumour agents. Particular attention was given to such drugs as Tacrolimus, Paclitaxel, Sirolimus, Dexamethasone, Estradiol, Cilostazol, Talidomide and analogues and derivatives thereof.

The quantity of the at least one active principle present in the composition is preferably comprised between 20% and 50% (w/w) of the composition and more preferably between 40% and 50%.

Once again the fact is emphasised that the scope of the present description is in no way limited to these specific active principles because the compositions described herein have an excellent degree of compatibility with other types of active principles, such as for example hydrophilic compounds.

EXAMPLES

The compositions object of the present description were loaded on stents made of AISI 316 and cobalt chromium steel coated with a thin film of pure turbostratic carbon (Carbofilm™), where such film augments the biocompatibility and thromboresistance of the stent.

On their external surfaces the stents have reservoirs, in the form of pits, capable of containing the compositions.

The compositions described herein can in any case be used with any type of stent and any type of implantable device, such as for example prosthetic valves or balloons for angioplasty.

Example 1

Stent Loaded with Sirolimus:Cholesteryl Palmitate in a Ratio (w/w) of 50:50 (Comparative Example)

30 mg of Cholesteryl palmitate (fatty acid ester) were weighed in a pyrex glass container, suspended in pentane with mechanical agitation and 30 mg of Sirolimus added.

The suspension was maintained under a current of nitrogen for 5 hours. The product obtained is a white powder of particles of very different sizes, for which the powder was transferred to a mortar and ground for 2 minutes.

The composition was loaded—using ways known in the art—into the reservoirs of a stent.

The loaded stent was then subjected to a thermal stabilisation procedure exposing the stent to a temperature comprised between 85-95° C. in an oven for about 3 minutes followed by 3 minutes of cooling to ambient temperature so to stabilize/fix the composition in the reservoirs.

Example 2

Stent Loaded with Sirolimus:Cholesteryl Butyrate in a Ratio (w/w) of 50:50 (Comparative Example)

In a suitable pyrex glass container 30 mg of Cholesteryl palmitate (fatty acid ester) were weighed, suspended in pentane with mechanical agitation and 30 mg of Sirolimus added.

The suspension was maintained under a current of nitrogen for 5 hours. The product obtained is a white powder of particles of very different sizes, for which the powder was transferred to a mortar and ground for 2 minutes.

The composition was loaded—using ways known in the art—into the reservoirs of a stent.

The loaded stent was then subjected to a thermal stabilisation procedure exposing the stent to a temperature comprised between 90-105° C. in an oven for about 3 minutes followed by 3 minutes of cooling to ambient temperature so to stabilize/fix the composition in the reservoirs.

Example 3

Stent Loaded with Sirolimus:Ascorbyl Palmitate/Cholesteryl Palmate Mixture in a Ratio (w/w) of 50:50 (Comparative Example)

In a suitable pyrex glass container 75 mg or Cholesteryl palmitate and 25 mg of Ascorbyl palmitate (fatty acid esters) were physically mixed by geometric dilution To this physical mixture suspended in pentane under mechanical agitation, 100 mg of Sirolimus were added. Such suspension was maintained under a current of nitrogen for 5 hours. The product obtained is a slightly yellowish powder of particles of very different sizes, for which the powder was transferred to a mortar and ground for 2 minutes.

After preparation the composition was loaded—using ways known in the art—into the reservoirs of a stent.

The loaded stent was then subjected to a thermal stabilisation procedure exposing the stent to a temperature comprised between 115-120° C. in an oven for about 3 minutes followed by 3 minutes of cooling to ambient temperature so to stabilize/fix the composition in the reservoirs.

Example 4

Stent Loaded with Sirolimus:Stearic Acid/Palmitic Acid Mixture in a Ratio (w/w) of 50:50

Two different compositions were prepared containing two different mixtures of Stearic acid and Palmitic acid (fatty acids), the mixtures i) with a stearic acid/palmitic acid ratio (w/w) of 45:55 and mixture ii) with a stearic acid/palmitic acid ratio (w/w) of 97:3.

In a pyrex glass container the following were physically mixed by geometric dilution:
45 mg of stearic acid and 55 mg of palmitic acid for preparation of mixture i),
97 mg of stearic acid and 3 mg of palmitic acid for preparation of mixture ii),
In two pyrex glass containers 50 mg of mixture i) and 50 mg of mixture ii), respectively, were weighed and suspended in pentane under mechanical agitation.

To each container 50 mg of Sirolimus were added.

The suspensions were maintained under a current of nitrogen for 5 hours. The product obtained is a fine white powder of particles of fairly uniform sizes, for which the powder was transferred to a mortar and ground for 1 minutes.

The two compositions i) and ii) were respectively loaded—using ways known in the art—into the reservoirs of two stents.

The two stents loaded with the two compositions were then subjected to a thermal stabilisation procedure exposing the stent to a temperature comprised between 65-80° C. in an oven for about 3 minutes followed by 3 minutes of cooling to ambient temperature so to stabilize/fix the composition in the reservoirs.

Example 5

Stent Loaded with Sirolimus:Stearic Acid/Palmitic Acid Mixture in a Ratio (w/w) of 45:55

In a suitable pyrex glass container 36 mg of a stearic acid/palmitic acid mixture in a ratio (w/w) of 97:3 were weighed, suspended in pentane under mechanical agitation and 30 mg of Sirolimus added.

The suspension was maintained under a current of nitrogen for 5 hours. The product obtained is a white powder with very uniform particle size. Nevertheless, the powder was transferred to a mortar and ground for 1 minute.

The composition was loaded—using ways known in the art—into the reservoirs of a stent.

The loaded stent was then subjected to a thermal stabilisation procedure exposing the stent to a temperature comprised between 65-80° C. in an oven for about 3 minutes followed by 3 minutes of cooling to ambient temperature so to stabilize/fix the composition in the reservoirs.

Example 6

Stent Loaded with Estradiol:Stearic Acid/Palmitic Acid Mixture in a Ratio (w/w) of 45:55

In a suitable pyrex glass container 36 mg of a stearic acid/palmitic acid mixture in a ratio (w/w) of 97:3 were weighed, suspended in pentane under mechanical agitation and 30 mg of Estradiol added.

The suspension was maintained under a current of nitrogen for 5 hours. The product obtained is a fine white powder of particles of fairly uniform sizes, and so the powder was transferred to a mortar and ground for 1 minute.

The composition was loaded—using ways known in the art—into the reservoirs of a stent.

The loaded stent was then subjected to a thermal stabilisation procedure exposing the stent to a temperature comprised between 65-80° C. in an oven for about 3 minutes followed by 3 minutes of cooling to ambient temperature so to stabilize/fix the composition in the reservoirs.

Example 7

Stent Loaded with Dexamethasone:Stearic Acid/Palmitic Acid Mixture in a Ratio (w/w) of 45:55

In a suitable pyrex glass container 36 mg of a stearic acid/palmitic acid mixture in a ratio (w/w) of 97:3 were weighed, suspended in pentane under mechanical agitation and 30 mg of Dexamethasone added.

The suspension was maintained under a current of nitrogen for 5 hours. The product obtained is a fine white powder of particles of fairly uniform sizes, and so the powder was transferred to a mortar and ground for 1 minutes.

The composition was loaded—using ways known in the art—into the reservoirs of a stent.

The loaded stent was then subjected to a thermal stabilisation procedure exposing the stent to a temperature comprised between 65-80° C. in an oven for about 3 minutes followed by 3 minutes of cooling to ambient temperature so to stabilize/fix the composition in the reservoirs.

Example 8

Microscopic Analysis of the Loaded Stents

After the stabilisation procedure by heat treatment, the stents prepared according to examples 1 to 7 were observed under an optical microscope.

In the case of the stents loaded with compositions including a fatty acid ester as the excipient (examples 1 to 3), microscopic analysis revealed that the compositions contained in the reservoirs have a heterogeneous/porous structure, i.e., micro/macro aggregates and cavities/pores. In particular, the stent in example 3 has molecular macro aggregates and yellowish formations.

On the contrary, for the stents with compositions including one or more fatty acid as excipient (examples 4 to 7), microscopic analysis revealed that the compositions have a homogeneous structure, i.e., are substantially free of molecular aggregates and/or cavities/pores.

Example 9

Differential Scanning Thermal Analysis

2 mg of the compositions for stent loading described in examples 1, 2 and 4 to 7 were placed in aluminium pans and then analysed by means of a TA Instruments Q100 with a 10° C./minute ramp.

Table 1 presents the endset temperatures (temperature at which the first fusion phenomena were complete) of the different compositions.

TABLE 1

| Composition | Temperature (° C.) |
| --- | --- |
| Example 1: | 83 |
| Example 2: | 106 |
| Example 4 - comp. i) | 66 |
| Example 4 - comp. ii) | 74 |
| Example 5: | 75 |
| Example 6: | 75 |
| Example 7: | 75 |

The compositions in examples 4 to 7 have thermal fusion phenomena that are completed at lower temperatures with respect to the compositions in examples 1 and 2. The experimental results support the use of an operative interval of 65-80° C. for stabilisation of the compositions in examples 4 to 7 on the stents.

Example 10

Verification of Drug Stability after Loading on Stents

During the production process of a device for coronary angioplasty, the stent loaded with a pharmaceutical formulation must in any case undergo further operations, such as assembly on catheters and sterilisation, which can be detrimental to the stability of the pharmaceutical formulation (exposure to temperatures up to 60° C., to humidity and to ethylene oxide. To verify the reliability and processability of the stents both in the preparative phase and in the successive completion of the device the following test was performed.

At the end of the stabilisation procedure by heat treatment, the stents made according to example 3 (fatty acid esters ascorbyl palmitate/cholesteryl palmitate) and according to example 5 (stearic and palmitic acids) were placed in an oven at 60° C. for 30 minutes. They were then immersed in acetonitrile and the solution obtained thusly was analysed using a Perkin Elmer Lambda 35 spectrophotometer to quantify the drug with respect to a calibration curve at the maximum absorbance peak of the drug at 277-278 nm.

The percent recovery of the drug loaded on stents made according to example 3 was 81%, while 97% of the drug was recovered from stents made according to example 5.

The difference in percent recovery of the drug for the stents made with fatty acid esters (example 3) with respect to those prepared with non-esterified fatty acids (example 5) shows the greater stability of the compositions object of the present description during the production process of a stent.

Example 11

Recrystallisation Temperature of the Active Principle

The recrystallisation temperature of the various active principle:excipient(s) compositions prepared as described in examples 1, 2 and 4 to 7 were determined using a TA Instruments Q100 with a 20° C./minute cooling ramp starting from the temperature indicated in table 1.

The results are presented in table 2.

TABLE 2

| Composition | Temperature (° C.) |
| --- | --- |
| Example 1: | 73 |
| Example 2: | 91 |
| Example 4 - comp. i) | 54 |
| Example 4 - comp. ii) | 64 |
| Example 5: | 64 |
| Example 6: | 64 |
| Example 7: | 65 |

Metallic stents by nature have optimal heat conduction, therefore when the stent is subjected to heat treatment and then placed at ambient temperature heat dispersion is extremely rapid. The use of one or more fatty acids as excipients in the compositions for loading on stents (examples 4 to 7) provides cooling of the composition inside the reservoirs of the stent that is slower with respect to that with fatty acid esters (examples 1 and 2), which start at higher fusion temperatures. A slower cooling velocity provides more favourable conditions for crystalline reorganisation of the drug and of the excipients.

Example 12

Preparation of a Stent Loaded with Amorphous Drug (Comparative Example)

A solution of Sirolimus in dioxane was deposited in the reservoirs of a stent using a micropipette of appropriate size.

The stent was placed in a vacuum dryer maintained at reduced pressure for 48 hours with a hydraulic pump so to remove the solvent completely.

A mixture of stearic/palmitic acids (97:3) in powder form was deposited onto the transparent solid film of drug that had been deposited at the bottom of the reservoirs of the stent. Once any excipient residue was removed from the external surface of the stent with a high-pressure nitrogen flow, the fatty acid mixture was stabilised inside the reservoirs through heat treatment in the interval comprised between 65-80° C. and successive cooling to ambient temperature.

Example 13

Dissolution In Vitro

The dissolution experiments were conducted measuring the quantity of drug released from the stent as a function of time.

In vitro dissolution analysis was performed on three compositions, the first two containing fatty acid esters as excipient, the third a fatty acid:
 i) Sirolimus:Cholesteryl palmitate in a ratio (w/w) of 45:55;
 ii) Sirolimus:Cholesteryl butyrate in a ratio (w/w) of 45:55;
 iii) Sirolimus: palmitic/stearic acid (3:97) in a ratio (w/w) of 45:55

The stents loaded with compositions i) to iii) and sterilised were expanded (applying the methods normally used in the procedure for implantation of a stent in the vascular system of a patient), fitted onto a small nylon spindle and immersed in the dissolution medium in a glass vial.

The operating condition are:
 Dissolution medium: acetate buffer pH 4.8 with 0.08% SDS (sodium dodecylsulfate);
 Shaking water bath thermostated at 37° C.; 80 oscillations per minute.
 complete replacement of the dissolution medium at every sampling;
 quantitative analysis of the drug using a Perkin Elmer Lambda 35 spectrophotometer with a calibration curve based on the maximum absorbance peak of the drug at 277-278 nm;
 construction of the cumulative release curve over time.

At the end of the dissolution experiments the reservoirs of the stents were observed microscopically at a magnification of 40× and were found to be completely empty.

As is shown in FIG. 1, when a mixture of stearic/palmitic fatty acids is used in the composition with the drug, the percent release in vitro is modulated differently from the compositions with the same drug:excipient ratio, but in which cholesteryl palmitate or cholesteryl butyrate is used as the excipient The use as excipient in the composition for loading on a stent of fatty acid(s) provides slower release kinetics with respect to compositions containing fatty acid esters.

This effect results both from the used of fatty acids as excipients, and by the reduced solubility of the drug in crystalline form.

In particular, the effect of reduced drug solubility in the crystalline form was confirmed comparing—with the same dissolution method—compositions loaded on stents in which the drug Sirolimus is in the form of crystalline nanoclusters as described in examples 4 and 5 or in the amorphous form as described in example 12.

Figure 2:
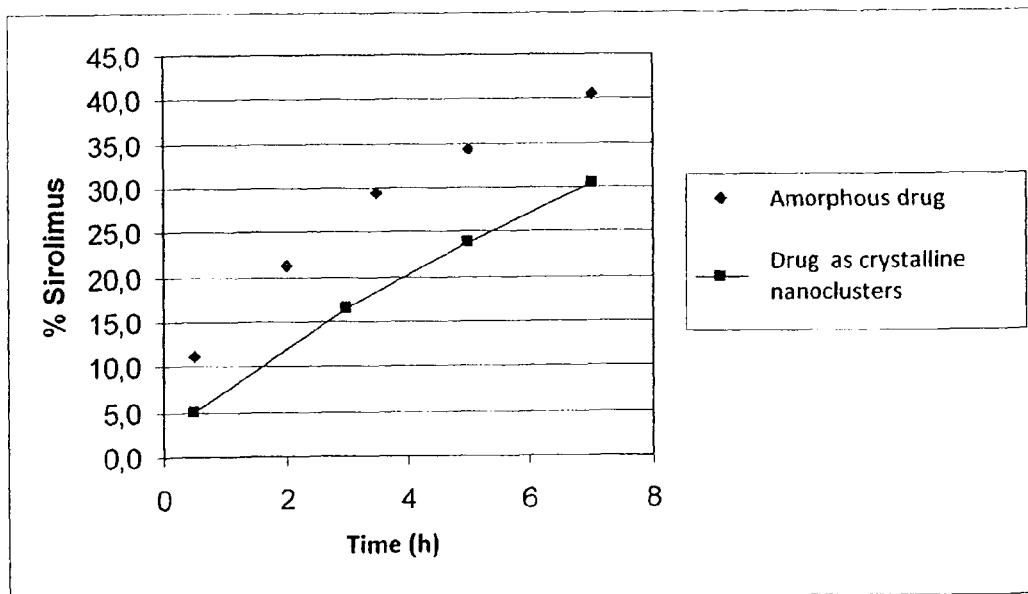
FIG. 2: Delivery profile of two compositions, amorphous Sirolimus:Stearic acid/Palmitic acid and crystalline Sirolimus:Stearic acid/Palmitic acid, loaded on metallic stents.

FIG. 2 shows that the drug release rate in crystalline nanoclusters is lower with respect to the release times of the drug in amorphous form.

Example 14

X-Ray Analysis

Analysis with x-rays identified the crystalline pattern of the Sirolimus:stearic/palmitic acid mixture composition prepared as described in example 5 and the amorphous pattern of the Sirolimus composition deposited by micropipette (example 12).

A sample of the Sirolimus:stearic/palmitic acid mixture composition 45:55 was stabilised with heat treatment at 76-78° C. and successively cooled to ambient temperature on a metallic support coated with Carbofilm™.

Figure 3:
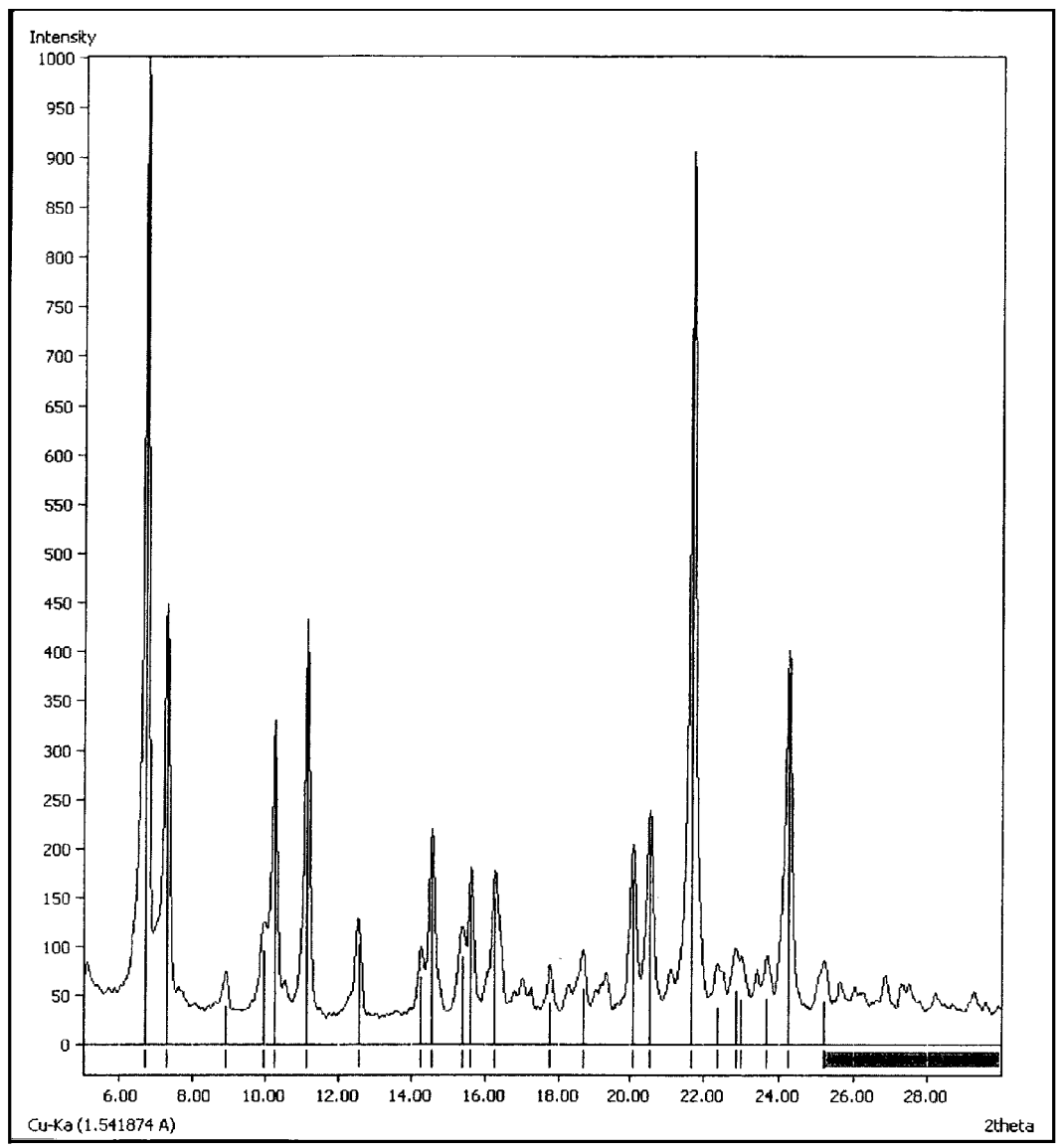
FIG. 3: X-ray diffraction spectrum of the Sirolimus:stearic/palmitic acid mixture composition with a ratio (w/w) of 45:55 deposited on a turbostratic carbon (Carbofilm™)-coated metallic support and stabilised by means of thermal treatment at 76-78° C. and successive cooling to ambient temperature.

The x-ray diffraction spectrum (recorded with a Rigaku DMAX powder diffractometer, Cu-K radiation, monochromator on the diffracted beam) of the Sirolimus:stearic/palmitic acid mixture illustrated in FIG. 3 reveals a crystalline pattern in which the identifying signals of two single components are clearly recognizable:

$2\theta°\sim6.70$ for stearic acid and
$2\theta°\sim7.30$ for Sirolimus.

Figure 4:
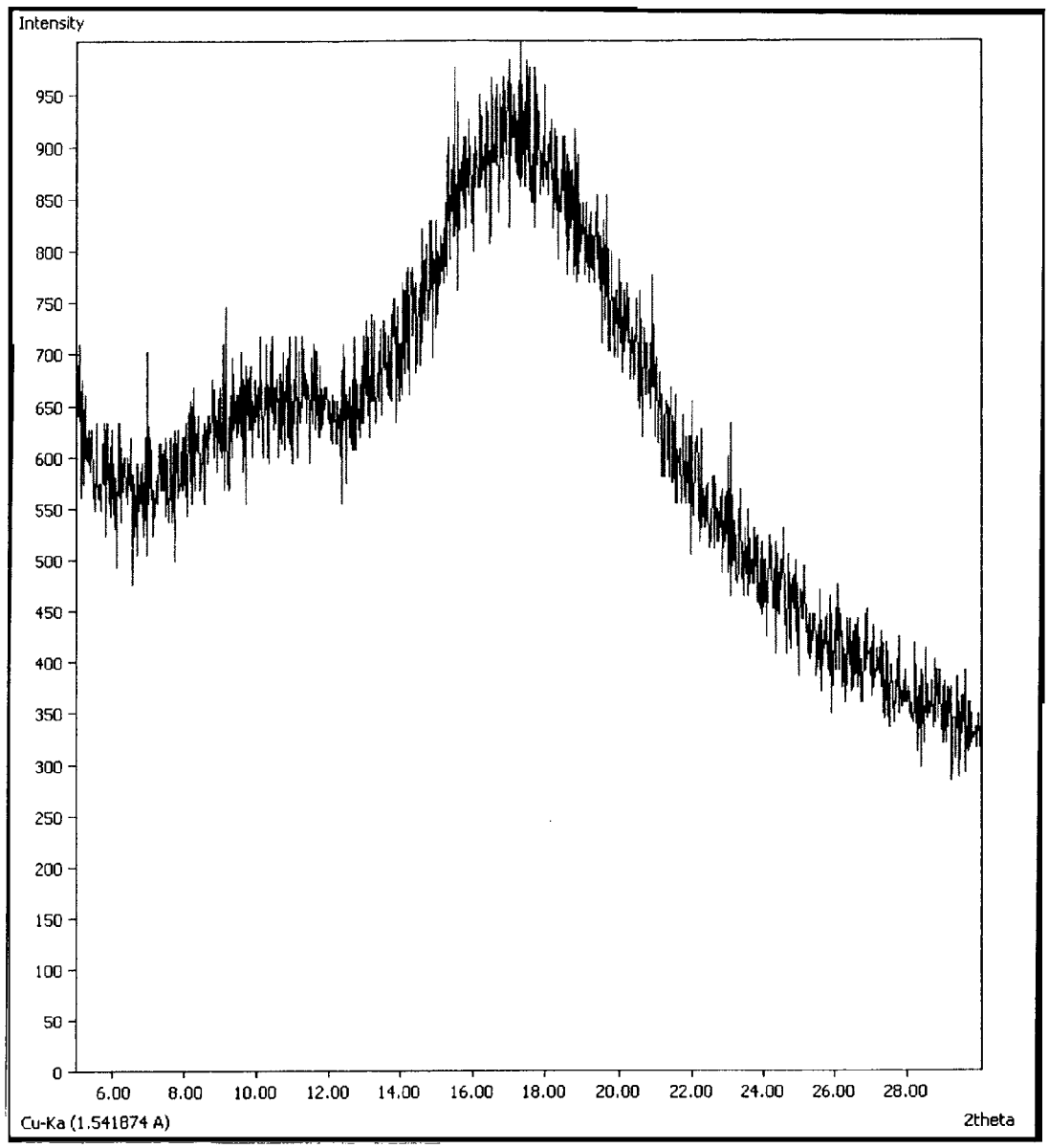
FIG. 4: X-ray diffraction spectrum of amorphous Sirolimus stabilised on a metallic support completely coated with turbostratic carbon (Carbofilm™) by depositing a Sirolimus solution in dioxane with an appropriately sized micropipette and successive drying under reduced pressure for 48 hours.

In the case of Sirolimus deposited with a micropipette and left to dry under vacuum no crystalline pattern is present, as is shown in FIG. 4.

Naturally, the details of implementation and the embodiments may vary widely with respect to what is described and illustrated without thereby departing from the field of protection of the present invention, as defined in the annexed claims.

The invention claimed is:

1. Composition for delivery of one or more active principles at the implantation site of an implant device, the composition consisting essentially of:
    said one or more active principles,
    one or more first excipients combined with said one or more active principles, wherein said one or more first excipients are selected from saturated fatty acids with a linear or branched chain having a number of carbon atoms between 14 and 36, and
    one or more second excipients different from said one or more first excipients and combined with said one or more active principles, wherein said one or more second excipients are selected from saturated fatty acids with a linear or branched chain having a number of carbon atoms between 14 and 36.

2. Composition according to claim 1, wherein said one or more first excipients are selected from stearic acid, palmitic acid, myristic acid, arachic acid, behenic acid, and melissic acid.

3. Composition according to claim 1, wherein said one or more second excipients are selected from stearic acid, palmitic acid, myristic acid, arachic acid, behenic acid, and melissic acid.

4. Composition according to claim 1, wherein said one or more first excipients are selected from stearic acid and behenic acid.

5. Composition according to claim 1, wherein said one or more second excipients are selected from palmitic acid and myristic acid.

6. Composition according to claim 1, loaded onto said implant device and subjected to a stabilization phase through a heat treatment, wherein said stabilized composition comprises at least one active principle in a crystalline form.

7. Composition according to claim 1, loaded onto said implant device and subjected to a stabilization phase through a heat treatment, wherein said stabilized composition comprises said one or more first excipients in a crystalline form.

8. Composition according to claim 6, wherein said heat treatment is carried out at a temperature between 65 and 80° C.

9. Composition according to claim 1, wherein said at least one or more active principles are present in an amount between 20% and 50% by weight of said composition.

10. Composition according to claim 1, wherein said one or more active principles are selected from anti-inflammatory agents, antiproliferative agents, promoters of wound healing, corticosteroids, tyrosine kinase inhibitors, immunosuppressants, and anticancer agents.

11. Composition according to claim 1, wherein said one or more active principles are selected from Tacrolimus, Paclitaxel, Sirolimus, Dexamethasone, Estradiol, Cilostazol, Thalidomide, their analogues or derivatives.

12. Composition according to claim 1, wherein said delivery of said one or more active principles occurs for a period of 3 to 140 days.

13. Implant device having loaded thereon a composition according to claim 1, wherein said implant device is selected from a stent, angioplasty balloon or prosthetic valve.

14. A method of delivering one or more active principles at the implantation site of an implant device comprising implanting into a patient at the implantation site an implant device having loaded thereon a composition consisting essentially of:
    one or more active principles to be delivered at the implantation site of an implant device,
    one or more first excipients combined with said one or more active principles, wherein said one or more first excipients are selected from saturated fatty acids with a linear or branched chain having a number of carbon atoms between 14 and 36, and
    one or more second excipients different from said one or more first excipients and combined with said one or more active principles, wherein said one or more second excipients are selected from saturated fatty acids with a linear or branched chain having a number of carbon atoms between 14 and 36.

15. Composition according to claim 1, the composition consisting of said one or more active principles, said one or more first excipients, and one or more second excipients.

16. Composition according to claim 7, wherein said stabilized composition comprises said one or more second excipients in a crystalline form.

17. Composition according to claim 9, wherein said one or more active principles are present in an amount between 45% and 50% by weight of said composition.

18. Composition according to claim 1, wherein said one or more active principles are selected from Tacrolimus, Paclitaxel, Sirolimus, Dexamethasone, Estradiol, Cilostazol, and Thalidomide.

* * * * *